United States Patent [19]

Sendo et al.

[11] Patent Number: 5,360,798
[45] Date of Patent: Nov. 1, 1994

[54] AMINOOXYPYRROLIDINYLTHIOCARBAPENEM COMPOUNDS

[75] Inventors: Yuji Sendo; Kii Makoto, both of Hyogo, Japan

[73] Assignee: Shionogi Seiyaku Kabushiki Kaisha, Osaka, Japan

[21] Appl. No.: 896,669

[22] Filed: Jun. 10, 1992

[30] Foreign Application Priority Data

Jul. 4, 1991 [JP] Japan ........................... 164247

[51] Int. Cl.$^5$ ................ C07D 487/04; A61F 31/40
[52] U.S. Cl. ............................... 514/210; 540/350
[58] Field of Search ............... 540/350, 310; 514/210

[56] References Cited

U.S. PATENT DOCUMENTS 4,983,596 1/1991 Murata et al. ............... 514/210
5,093,328 3/1992 Sunagawa et al. ............ 540/350

OTHER PUBLICATIONS

Chemical Abstracts vol. 18 (23) 233767(a) 1994.

*Primary Examiner*—Nicholas S. Rizzo
*Attorney, Agent, or Firm*—Birch, Stewart Kolasch & Birch

[57] ABSTRACT

An antibacterial aminooxypyrrolidinylthiocarbapenem I, its production from the corresponding carbapenem V and thiol VI, its pharmaceutical formulation, and its use or combating bacteria are presented.

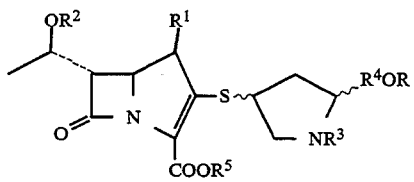

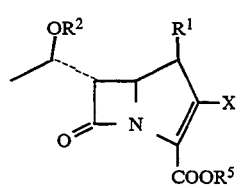

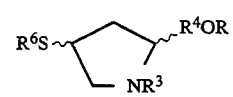

(wherein R is optionally substituted amino; $R^1$ is hydrogen or 1C to 5C alkyl; $R^2$ is hydrogen or a conventional hydroxy protective group; $R^3$ is hydrogen or an imino protective group or imino substituent; $R^4$ is 1C to 5C alkylene; and $R^5$ is hydrogen or a conventional carboxy protective group; X is a leaving group; $R^6$ is hydrogen or a thiol protective group; and wavy lines each shows a bond in R or S configuration).

17 Claims, No Drawings

AMINOOXYPYRROLIDINYLTHIOCARBAPENEM COMPOUNDS

This invention relates to novel carbapenem antibacterials. More specifically, it relates to aminooxypyrrolidinylthiocarbapenems of Formula I and their salt:

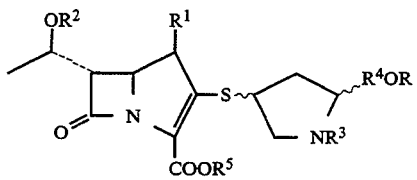

(wherein R is an optionally substituted amino; $R^1$ is hydrogen or 1C to 5C alkyl; $R^2$ is hydrogen or a conventional hydroxy protecting group; $R^3$ is hydrogen or an imino protecting group or an imino substituent: $R^4$ is a 1C to 5C alkylene: and $R^5$ is hydrogen or a conventional carboxy protecting group; and each of the wavy lines shows a bond which is an in R or S configuration Y.

Several carbapenem antibacterials having a pyrrolidinylthio group at the position 2 are known {e.g., (5R,6S)-2-[1-(1-acetoimidoyl)pyrrolidin-3-ylthio]-6-[(1R)-1-hydroxy-ethyl]carba-2-penem-3-carboxylic acid (CS533), (1R,5S,6S)-2-[(3S,5S)-5-dimethylaminocarbonylpyrrolidin-3-ylthio]-6-[(1R)-1-hydroxyethyl]-1-methyl-1-carba-2-penem-3-carboxylic acid (Meropenem), (1R,5S,6S)-2-[6,7-dihydro-5H-pyrazolo[1,2-a]-(1,2,4-triazolium-6-yl)thio]-6-[(1R)-1-hydroxyethyl]-1-methyl-1-carba-2-penem-3-carboxylic acid (LJC-10627), (1R,5S,6S)-2-[(3S,5S)-5-methanesulfonylaminomethylpyrrolidin-3-ylthio]-6-[(1R)-1-hydroxyethyl]-1-methyl-1-carba-2-penem-3-carboxylic acid (Japanese Patent Publication Kokai Showa-63-179876)}. However, new potent antibacterials are always demanded to cope with the appearance of new resistant strains of bacteria.

The present inventors while working to develop useful carbapenem antibacterials, synthesized novel Compounds of Formula I having a pyrrolidinylthio group substituted by a unique aminooxyalkyl substituent at position 2. Compounds I are excellent antibacterial activity in vitro against Gram-negative bacteria, excellent physico dynamic characteristics, excellent therapeutical effects for treating bacterial infections, and high chemical and metabolic properties in vivo.

The following definitions are provided for the compounds of this invention, etc.

In this specification, the substituent in the optionally substituted amino R can be a 1C to 10C monovalent amino substituent (e.g., alkyl, acyl, alkoxycarbonyl, optionally substituted carbamoyl, alkylsulfonyl, optionally substituted sulfamoyl; especially methyl, acetyl, carbomethoxy, N-methylcarbamoyl, methanesulfonyl, sulfamoyl) and a 1C to 10C divalent amino substituent (e.g., alkylidene, cyclic diacyl; especially ethylidene, phthalyl). R may have one or two of the said monovalent amino substituents or one of the said divalent amino substituents.

The alkyl is a 1C to 10C straight or branched chain saturated hydrocarbon group (e.g., methyl, ethyl, n-propyl, isopropyl, butyl, isobutyl, sec-butyl, tert-butyl, pentyl, isopentyl, neopentyl, 1,2-dimethylbutyl, hexyl, heptyl, octyl).

The alkylene is a straight or branched 1C to 5C divalent hydrocarbon group (e.g., methylene, ethylene, propylene).

The substituent $R^3$ is a 1C to 19C imino protective group including 1C to 8C alkyl (e.g., trichloroethyl, methoxyethoxymethyl, tetrahydropyranyl), 7C to 19C aralkyl (e.g., triphenylmethyl, methoxybenzyl), 1C to 8C alkylthio, 6C to 8C arylthio (e.g., nitrophenylthio), 1C to 8C acyl [e.g., 1C to 8C alkanoyl (e.g., formyl, acetyl, chloroacetyl), 2C to 8C alkoxycarbonyl (e.g., having methyl, ethyl, cyclopropylmethyl, cyclopropylethyl, isopropyl, butyl, isobutyl, hexyl, trichloroethyl, pyridylmethyl, or cyclohexyl as alkoxy), 8C to 19C aralkoxycarbonyl (e.g., those having benzyloxy, diphenylmethyloxyoxy, or nitrobenzyloxy as aralkoxy), 7C to 12C aroyl (e.g., benzoyl, nitrobenzoyl)], 3C to 9C trialkylsilyl, 1C to 5C amidino (e.g., amidino, dialkylamidino). or the like.

The hydroxy protective group is an easily removable 1C to 19C ester forming group [carboxylic acyl, for example, lower alkanoyl (e.g., formyl, acetyl, propionyl, pivaloyl), aroyl. e.g., benzoyl, toluoyl, xyloyl), 2C to 10C alkoxycarbonyl (e.g., t-butoxycarbonyl, cyclopropylmethyloxycarbonyl), 8C to 15C aralkoxycarbonyl (e.g., benzyloxycarbonyl, 4-nitrobenzyloxycarbonyl, 4-methoxybenzyloxycarbonyl)], an easily removable 2C to 8C ether forming group (e.g. tetrahydropyranyl, tetrahydrofuranyl, methoxymethyl, methoxyethoxymethyl), or 3C to 10C hydrocarbylsilyl (e.g., trimethylsilyl, triethylsilyl, t-butyldimethylsilyl).

The carboxy protective group can be those for synthetic purposes containing 1 to 19 carbon atoms known in this art as those introducable and removable without adverse effect on other parts of the molecule. Representative ester forming groups, are e.g., 1C to 8C alkyl (e.g., methyl, methoxymethyl, ethyl, ethoxymethyl, iodoethyl, propyl, isproyl, butyl, isobutyl, ethoxyethyl, methylthioethyl, methanesulfonylethyl, trichloroethyl, t-butyl), 3C to 8C alkenyl (e.g., propenyl, allyl, prenyl, hexenyl, phenylpropenyl. dimethylhexenyl), 7C to 19C aralkyl (e.g., benzyl, methylbenzyl, dimethylbenzyl, methoxybenzyl, ethoxybenzyl, nitrobenzyl, aminobenzyl, diphenylmethyl, phenethyl, trityl, di-t-butylhydroxybenzyl, phthalidyl, phenacyl), 6C to 12C aryl (e.g., phenyl, tolyl, diisopropylphenyl, xylyl, trichlorophenyl, pentachlorophenyl, indanyl), 1C to 12C amino (e.g., forming an ester with acetone oxime, acetophenone oxime, acetaldoxime, N-hydroxysuccinimide, N-hydroxyphthalimide), 1-oxygenated-2C to 15C alkyl {e.g., straight, branched, cyclic, or partially cyclic alkanoyloxyalkyl (e.g., acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl), 3C to 15C alkoxycarbonyloxyalkyl (e.g., ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl), 2C to 8C alkoxyalkyl (e.g., methoxymethyl, methoxyethyl), 4C to 8C 2-oxacycloalkyl alkyl (e.g., tetrahydropyranyl, tetrahydrofuranyl)}, 8C to 12C aralkyl (e.g., phenacyl, phthalidyl), 6C to 12C aryl (e.g., phenyl, xylyl, indanyl), 2C to 12C alkenyl (e.g., allyl, prenyl, 2-oxo-1,3-dioxol-4-ylmethyl), or the like.

The salt at $R^5$ is preferably a light metal forming a pharmaceutically acceptable ion conventional in the penicillin and cephalosporin fields and belonging to group I to III and period 2 to 4 in the Periodical Table, for example, an alkali metal (e.g., sodium, potassium, lithium), an alkaline earth metal (e.g., magnesium, calcium), aluminum, or the like. Ammonium salt at $R^5$ is preferably a salt with 1C to 12C alkylamine (e.g., trimethylamine, triethylamine, methylmorpholine) or 4C to 9C aromatic base (e.g., pyridine, collidine, picoline, quinoline). The acid for an acid addition salt at R or $R^3$ is a pharmaceutically acceptable mineral acid (e.g., nitric acid, hydrochloric acid, sulfuric acid), or 1C to 5C organic acid (e.g., citric acid, succinic acid).

These groups can further be substituted.

Compounds I are all useful for the purpose of this invention. Especially useful are the followings and their alkali metal salts in which the stereochemistry in the pyrrolidine ring is (2S,4R)- or (2S, 4S)-: i.e., R is amino, $R^1$ is methyl, R'and $R^3$ are hydrogens, $R^4$ is methylene, and $R^5$ is hydrogen; R is acetylamino, $R^1$ is methyl, $R^2$ and $R^3$ are hydrogens, $R^4$ is methylene, and $R^5$ is hydrogen; R is carbomethoxyamino, $R^1$ is methyl, $R^2$ and $R^3$ are hydrogens, $R^4$ is methylene, and $R^5$ is hydrogen; R is methylcarbamoylamino, $R^1$ is methyl, $R^2$ and $R^3$ are hydrogens, $R^4$ is methylene, and $R^5$ is hydrogen; R is methanesulfonylamino, $R^1$ is methyl, $R^2$ and $R^3$ are hydrogens, $R^4$ is methylene, and $R^5$ is hydrogen; R is sulfamoylamino, $R^1$ is methyl, $R^2$ and $R^3$ are hydrogens, $R^4$ is methylene, and $R^5$ is hydrogen; R is methylamino, $R^1$ is methyl, R'and $R^3$ are hydrogens, $R^4$ is methylene, and $R^5$ is hydrogen; and R is ethylideneamino, $R^1$ is methyl, $R^2$ and $R^3$ are hydrogens, $R^4$ is methylene, and $R^5$ is hydrogen.

This invention also provides a method for producing Compound I by condensing a carbapenem V or its reactive derivative with a novel thiol VI ($R^6$=H) or its reactive derivative followed by optional deprotection or modification.

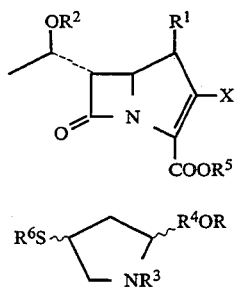

(wherein R, $R^1$, $R^2$, $R^3$, $R^4$, and $R^5$ are as defined in claim 1, X is a leaving group, and $R^6$ is hydrogen or a thiol protective group) The leaving group X in carbapenem V is conventional in the art and can be a 1C to 8C alkanesulfonyloxy (e.g., methanesulfonyloxy, trifluorosulfonyloxy), a 6C to 10C arylsulfonyloxy (e.g., phenylsulfonyloxy, bromobenzenesulfonyloxy, toluenesulfonyloxy), phosphoryloxy (diphenylphosphoryloxy), or a 1C to 8C sulfinyl (e.g., ethylsulfinyl, phenylsulfinyl). The starting carbapenem V or its production is known.

This invention further provides novel pyrrolidinylthiol VI, a useful intermediate for producing useful carbapenems. Thiol VI is prepared from D- or L-hydroxyproline by combining the following steps in an order suitable for conventional reactions: 1) Protecting the ring nitrogen (e.g., t-butoxycarbonyl, p-nitrobenzyloxycarbonyl with the corresponding chloride or anhydride and an organic base), 2) Activating the hydroxy for substitution to thiol (e.g., esterification with alkane or arylsulfonic acid chloride to form a leaving group), 3) Substituting the activated hydroxy with a sulfur function (e.g., triphenylmethylthiol with sodium salt), 4) Reducing the carboxy to methylol (e.g., with alkali metal borohydride), if required after activation (e.g., esterification with lower alkanol), 5) Introducing amino to the methylol (e.g., with N-hydroxyphthalimide), if required followed by deprotection (e.g., with hydrazine) or modification at amino as R to form the desired $R^4OR$ group, and 6) Deprotecting at ring R, $R^3$, or thiol, if required. Preferably $R^6$ is 1C to 10C alkanoyl (e.g., acetyl, isobutyryl), a 7C to 10C aroyl (e.g., benzoyl, toluoyl), or a 7C to 19C aralkyl (e.g., trityl, or benzhydryl).

Carbapenem V and thiol VI are condensed in a conventional manner in an aprotic polar solvent (e.g., acetonitrile) in the presence of tertiary amine (e.g., diisopropylamine) at a low temperature, for example, $-50°$ to $+30°$ C. (preferably $-40°$ to $10°$ C.) for 10 minutes to 10 hours (preferably 30 minutes to 5 hours).

The product is subjected to deprotection, modification at ring nitrogen, etc. to obtain the desired Compounds I. The deprotection can be done in a conventional manner for producing carbapenem compounds. For example, p-nitrobenzyl ester as $R^5$ is removed in a mixture of tetrahydrofuran and 2-(morpholin-4-yl)ethanesulfonic acid buffer solution by catalytic hydrogenation using palladium on charcoal. Further, some carboxy protective ester group such as $R^5$ (e.g. allyl, isoprenyl, p-methoxybenzyl, diphenylmethyl) and an amino protective carbonate acyl group in R or an imino protective carbonic acyl group such as $R^3$ (e.g., t-butoxycarbonyl, allyloxycarbonyl, p-methoxybenzyloxycarbonyl) can be removed using 1 to 20 (preferably 2 to 15) equivalents of a Lewis acid (e.g., aluminum chloride, stannic chloride, titanium chloride) or a carboxylic acid (e.g., trifluoroacetic acid) in an aprotic solvent (e.g., dichloromethane, anisole, nitromethane) for 1 to 10 (preferably 1 to 5 hours) at $-40°$ to $10°$ (preferably $-30°$ to $0)°C$. A trialkylsilyl hydroxy protective group such as $R^1$ (e.g., trimethylsilyl, triethylsilyl, t-butyldimethylsilyl) can be removed with aqueous acid (e.g., hydrochloric acid or the like mineral acid).

A modification of ring imino, e.g., amidinio introduction, is as follows: To a solution of Compound I in a phosphate buffer of pH about 7 under ice cooling is added ethylformimidate hydrochloride in several portions while keeping the pH 8.5 with 1N-sodium hydroxide.

The work up of the reaction mixture is done in a conventional manner in the art to give the free acid, for example, removing unreacted reagent, purifing by crystallization, adsorption and elution, chromatography, lyophilization, etc.

Compounds I show potent antibacterial activity in vitro and good physico dynamic properties (e.g., urinary recovery, maximum blood level in mice, and stability to human renal dehydropeptidase 1) as compared with some known carbapenems. For example, Compounds I having R as methanesulfonylamino (M) or sulfamido (H) show the following improvements in percent over some known carbapenems:

vs. Imipenem: two times or more antibacterial activity in vitro against Gram-negative bacteria (e.g., *Escherichia coli* H, *Escherichia coil* SR 5028, *Klebsi-* ella pneumoniae SR1, Proteus mirabilis PR4, Morgania morganii SR9, Enterobacter cloacae SR233) (M, H), urinary recovery in mice (M:23%, H:44%), and stability against human renal dehydropeptidase-1 (M:53%, H:39%).

vs. Meropenem: urinary recovery (M:151%, H:192%), maximum blood level (M:62%, H:92%), protection of mice from *Streptococcus aureus* Smith infection (M:370%, H:1300%), and stability to human renal dehydropeptidase-1 (M:3%, H:13%).

vs. CS 533: two times or more antibacterial activity in vitro against Gram-negative bacteria (e.g., *Escherichia coli* H, *Escherichia coli* SR 5028, *Klebsiella pneumoniae* SR1, *Proteus mirabilis* PR4, *Morgania morganii* SR9) (M, H), maximum blood level (M:27%, H:51%), urinary recovery in mice (M:71%, H:99%), and stability to human renal dehydropeptidase-1 (M:63%, H:48%).

vs. LJ 10627: two times or more antibacterial activity in vitro against Gram-negative bacteria (e.g., *Proteus mirabilis* PR4, *Proteus vulgaris* CN-329, *Proteus vulgaris* SR3, *Morgan morganii* SR9, *Serratia marsescens* A13880) (M, H).

vs. a compound in Japanese Patent Publication Kokai 179876/1988: about two-fold antibacterial activity in vitro against *Staphylococcus aureus* SR 77 and *Morgania morganii* SR 9 (M).

Thus, Compounds I are useful as medicines, veterinary drugs, disinfectants, antiperishables, etc., and this invention provides an antibacterial agent containing the compound as an effective component and a disinfection method by contacting the compound with bacteria.

Compound I having $R^5$ as alkali metal is suitable for parenteral administration (e.g., intravenous injection, intramuscular injection, drip) and can be presented as an injection, vials, etc., if required accompanied by stabilizing and solubilizing agent. The free acid can form an aqueous solution by neutralization before administration. The esters can be used for oral administration as tablets, capsules, granules, powders, etc., for injection as a suspension, oily injection, etc., and for external and topical use as suppository, eye solution, ointment, emulsion, spray, etc. These preparations can be produced using conventional additives in a conventional manner.

An effective amount of compound I or its salt is given to an infected subject by way of, e.g., oral or parenteral route, although the latter is more preferable. For parenteral administration, the compound is formulated to afford an aqueous solution or suspension (suitable for, e.g., subcutaneous injection, intravenous injection, intraperitoneal injection, or intramuscular injection). For oral administration, Compound I as an acid or ester is mixed with a conventional formulation carrier, diluent, or additives and encapsulated or tabletted. It may be formulated to give a powder or granule in a conventional manner.

Preferably the daily dose is about 100 mg to 6 g (e.g., 250 mg to 3 g) for injection and about 100 mg to 6 g (e.g., 250 mg to 4 g) for oral use.

The following Examples and Experiment are given to illustrate this invention. These examples, however, are not intended to limit the scope of this invention.

The abbreviations are as follows:
Boc=t-butoxycarbonyl. Et=ethyl. Ft=phthalyl. Me=methyl. Pnz=p-nitrobenzyloxycarbonyl. Pmz=p-methoxybenzyloxycarbonyl. Tr=trityl. THF=tetrahydrofuran.

EXAMPLE 1

Synthesis of 3-substituent

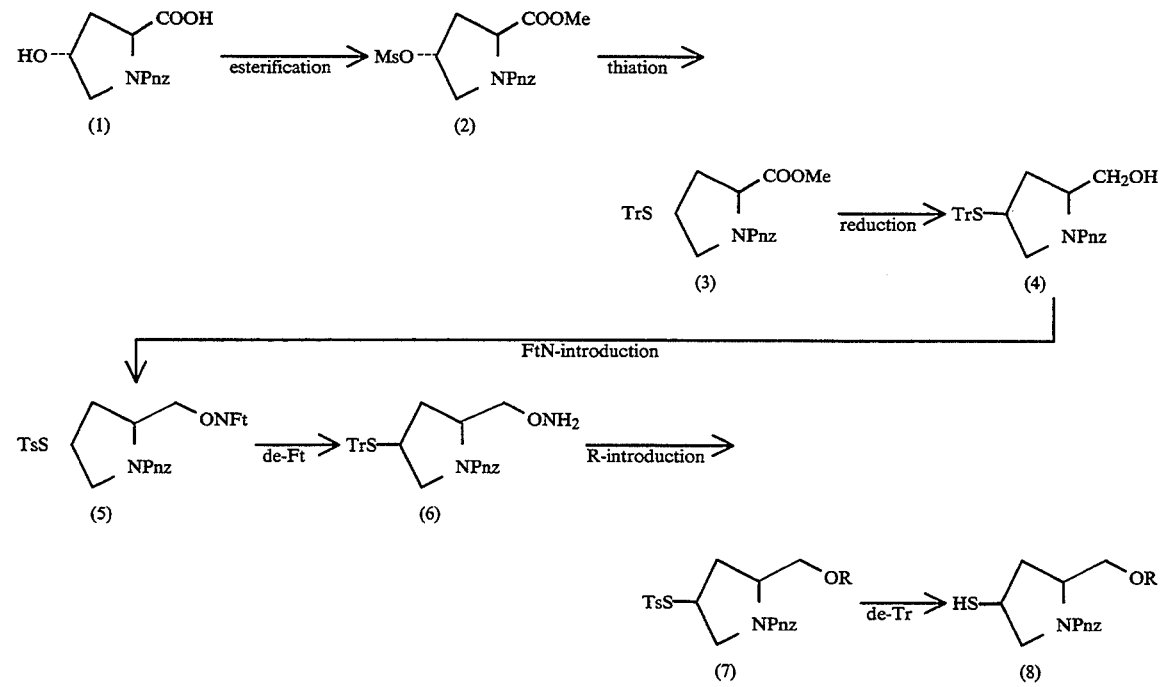

A. Preparation of protected thioaminooxymethylpyrrolidine 1) (2S,4R)-4-hydroxy-2-methoxycarbonyl-1-p-nitrobenzyloxycarbonylpyrrolidine (esterification)

To a mixture of methanol (94.5 ml) and dichloromethane (945 ml) under ice cooling are dropwise added thionyl chloride (18.7 ml) and after 5 minutes stirring N-p-nitrobenzyloxycarbonyl-L-hydroxyproline (1:72.4 g), and the mixture is stirred overnight at room temperature. The reaction mixture is concentrated in vacuum to give crude (2S,4R)-4-hydroxy-2-methoxycarbonyl-1-p-nitrobenzyloxycarbonylpyrrolidine (86.5 g) as pale yellow oil. This product can be used in the next step without further purification.

IR $\nu$ (CHCl$_3$) cm$^{-1}$: 3450, 1742, 1703, 1605. $^1$HNMR $\delta$ (CDCl$_3$) ppm: 1.77(1H, s), 2.05 to 2.45(2H, m), 3.55 to 3.8(2H, m), 3.60, 3.76(3H, 2s), 4.49 to 4.62(2H, m), 5.06 to 5.35(2H, m), 7.43 to 7.56(2H, m), 8.22(2H, d, J=8.2 Hz).

2) (2S,4R)-4-methanesulfonyloxy-2-methoxycarbonyl-1-p-nitrobenzyloxycarbonylpyrrolidine (2) (hydroxy activation)

To a solution of crude (2S,4R)-4-hydroxy-2-methoxycarbonyl-1-p-nitrobenzyloxycarbonylpyrrolidine (86.1 g) in dichloromethane (1 liter) under ice cooling are added triethylamine (52 ml) and then methanesulfonyl chloride (21.6 ml), and the mixture is stirred for 25 minutes. The reaction mixture is acidified with diluted hydrochloric acid and stirred. The organic layer is taken, washed with aqueous sodium hydrogen carbonate and water, dried over sodium sulfate, and concentrated in vacuo to give (2S, 4R)-4-methanesulfonyloxy-2-methoxycarbonyl-1-p-nitrobenzyloxycarbonylpyrrolidine (2:90.0 g) as an organge oil. This product can be used in the next step without further purification.

IR $\nu$ (CHCl$_3$) cm$^{-1}$: 1741, 1703, 1602. $^1$HNMR $\delta$ (CDCl$_3$) ppm: 2.22 to 2.82(2H, m), 3.07(3H, s), 3.67, 3.78(3H, 2s), 3.75 to 4.03(2H, m), 4.55(1H, t, J=7.8 Hz), 5.08 to 5.39(3H, m), 7.43 to 7.58(2H, m), 8.23(2H, d, J=8.6 Hz).

3) (2S,4S)-4-triphenylmethylthio-2-methoxycarbonyl-1-p-nitrobenzyloxycarbonylpyrrolidine (3) (thiolation)

To a suspension of sodium hydride (1.26 g) (60% dispersion in oil) in dimethylformamide (50 ml) under ice cooling is added triphenylmethylmercaptan (10.9 g) in small portions and stirred for 5 minutes at room temperature. A solution of crude (2S,4R)-4-methanesulfonyloxy-2-methoxycarbonyl-1-p-nitrobenzyloxycarbonylpyrrolidine (2:10.6 g) in dimethylformamide (80 ml) is added to this mixture, and the whole mixture is stirred in an oil bath at 50° C. overnight. The reaction mixture is diluted with ethyl acetate and mixed with ice water containing 1N-hydrochloric acid (35 ml). The organic layer is taken, washed with water and satd. brine, dried over sodium sulfate, and concentrated in vacuo. The residue is purified by silica gel chromatography (toluene-ethyl acetate) to give (2S ,4S)-4-triphenylmethylthio-2-methoxycarbonyl-1-p-nitrobenzyloxycarbonylpyrrolidine (3:9.12 g) an orange foam (Yield: 52% from hydroxyproline) and the starting compound (2:3.11 g: Yield: 29%).

IR $\nu$ (CHCl$_3$) cm$^{-1}$: 1745, 1702, 1602. $^1$HNMR $\delta$ (CDCl$_3$) ppm: 1.64 to 2.36(2H, m), 2.68 to 3.32(2H, m), 3.32 to 3.55(1H, m), 3.61, 3.65, 3.72(3H, 3s), 4.01 to 4.27(1H, m), 4.95 to 5.32(2H, m), 7.15 to 7.53(17H, m), 8.14 to 8.27(2H, m).

4) (2S,4S)-4-triphenylmethylthio-2-hydroxymethyl-1-p-nitrobenzyloxycarbonylpyrrolidine (Reduction of carbomethoxy)

To a solution of (2S,4S)-4-triphenylmethylthio-2-methoxycarbonyl-1-p-nitrobenzyloxycarbonylpyrrolidine (3:3.63 g) in tetrahydrofuran (36 ml) under ice cooling are added a solution of sodium borohydride (371 mg) in ethanol (15 ml) and a solution of lithium chloride (554 mg) in tetra-hydrofuran (15 ml), and the mixture is warmed to room temperature and stirred for 110 minutes. The reaction mixture is diluted with ethyl acetate under ice cooling, neutralized with 1N-hydrochloric acid (10 ml) to decompose remaining reagent. The organic layer is taken, washed with water and saturated brine, dried over sodium sulfate, and concentrated in vacuo. The residue is purified by silica gel chromatography to give (2S,4S)-4-triphenylmethylthio-2-hydroxymethyl-1-p-nitrobenzyloxycarbonylpyrrolidine (4:3.02 g) as colorless foam. Yield: 88%.

IR $\nu$ (CHCl$_3$) cm$^{-1}$: 3400, 1679, 1603. $^1$HNMR $\delta$ (CDCl$_3$) ppm: 1.3 to 2.13(2H, m), 1.6(1H, brs), 2.65 to 4.3(6H, m), 5.03 to 5.2(2H, m), 7.07 to 7.55(17H, m), 8.15 to 8.3(2H, m).

5) (2S,4S)-4-triphenylmethylthio-2-phthalimidoxymethyl-1-p-nitrobenzyloxycarbonylpyrrolidine (5) (introduction of imidooxy)

To a solution of (2S,4S)-4-triphenylmethylthio-2-hydroxymethyl-1-p-nitrobenzyloxycarbonylpyrrolidine (4:555 mg) in tetrahydrofuran (6 ml) under ice cooling are added triphenylphosphine (315 mg), azodicarboxylic acid diethyl ester (189 $\mu$l) and after stirring for 5 minutes N-hydroxyphthalimide (196 mg), and the mixture is stirred for 45 minutes. The reaction mixture is concentrated in vacuo. The residue is purified by silica gel column chromatography to give (2S,4S)-4-triphenylmethylthio-2-phthalimidoyloxymethyl-1-p-nitrobenzyloxycarbonylpyrrolidine (5:686 mg) as a pale yellow foam. Yield: 98%.

IR $\nu$ (CHCl$_3$,) cm$^{-1}$: 1783, 1725, 1093, 1602. $^1$HNMR $\delta$ (CDCl$_3$) ppm: 1.8 to 2.5(2H, m), 2.5 to 3.0(2H, m), 3.15 to 3.54(1H, m), 3.94(1H, brs), 4.08 to 4.5(2H, m), 4.98 to 5.25(2H, m), 7.1 to 7.6(17H, m), 7.65 to 7.95 (4H, m), 8.0 to 8.3(2H, m).

6) (2S,4S)-4-triphenylmethylthio-2-aminooxymethyl-1-p-nitrobenzyloxycarbonylpyrrolidine (6) (removing phthalimido)

To a solution of (2S,4S)-4-triphenylmethylthio-2-phthalimidoyloxymethyl-1-p-nitrobenzyloxycarbonylpyrrolidine (5:501 mg) in dichloromethane (5 ml) at −40° C. is added methylhydrazine (42 $\mu$l), and the mixture is stirred for 5 minutes and then under ice cooling for 30 further minutes to give a solution of (2S,4S)-4-triphenylmethylthio-2-aminooxymethyl-1-p-nitrobenzyloxycarbonylpyrroline (6).

B. Introduction of amino substituent (2S,4S)-4-triphenylmethylthio-2-acetylaminooxymethyl-1-p-nitrobenzyloxycarbonylpyrrolidine (7a) (acetylation)

To a solution of (2S,4S)-4-triphenylmethylthio-2-aminooxymethyl-1-p-nitrobenzyloxycarbonylpyrrolidine (6), prepared as above A (6), in dichloromethane are added pyridine (93 $\mu$l) and acetyl chloride (66 $\mu$l), and the mixture is stirred for 25 minutes. To the reaction mixture are added 1N-hydrochloric acid (1 ml) and ethyl acetate. The organic layer brine, dried over sodium sulfate, and concentrated in vacuo. The residue is purified by silica gel chromatography to give (2S,4S)-4-triphenylmethylthio-2-acetylaminooxymethyl-1-p-nitrobenzyloxycarbonylpyrrolidine (7:385 mg) as a pale yellow foam. Yield: 88%;.

In a manner similar to B above, the amino substituent is introduced to aminooxypyrrolidine (6) produced in A(6) above under the condition given in Table 1 to give protected mercaptide. The producing condition for compounds 7a (prepared by B) to 7g is listed on Table 1.

TABLE 1

Reaction conditions for introducing amino substituent

|   | Reagent | equivalents | Solv. | Base | equivalents | Temp °C. | Time min. | Crop % |
|---|---|---|---|---|---|---|---|---|
| a | MeCOCl | 1.3 | $CH_2Cl_2$ | Py[1)] | 1.6 | 0 | 25 | 88 |
| b | $ClCO_2Me$ | 1.3 | $CH_2Cl_2$ | Py | 1.6 | 0 | 20 | 98 |
| c | MeNCO | 4.6 | $CH_2Cl_2$ |  |  | rt | 105 | 100 |
| d | $ClSO_2Me$ | 1.55 | $CH_2Cl_2$ | Py | 2.4 | 0 | 100 | 94 |
| e | $ClSO_2NHCO_2PMB$[2)] | 1.1 | $CH_2Cl_2$ | $Et_3N$ | 1.2 | 0 | 30 | 86 |
| f | MZ-SDP[3)] | 1.2 | $C_5H_6$ |  |  | refl | 100 | 60 |
| g | MeCHO | 5.0 | $CH_2Cl_2$ |  |  | 0 | 30 | 93 |

Note:
[1)]pyridine.
[2)]prepared from chlorosulfonyl isocyanate and p-methoxybenzyl alcohol.
[3)]S-p-methoxybenzyloxycarbonyl-4,6-dimethyl-2-mercaptopyrimidine.

Physical constants of protected mercaptide (7a to 7g)

Compound 7a R=acetylamino

IR ν (CHCl$_3$) cm$^{-1}$:3260, 1880, 1600. $^1$HNMR δ (CDCl$_3$) ppm: 1.3 to 2.37(2H, m), 1.87(3H, brs), 2.7 to 2.9(2H, m), 2.98 to 3.22(1H, m), 3.45 to 4.27(3H, m), 5.10, 5.17(2H, 2s), 7.07 to 7.54 (17H, m) 8.17 to 8.30(2H, m).

Compound 7b R=carbomethoxyamino

IR ν (CHCl$_3$) cm$^{-1}$: 3360, 1720, 1685, 1600. $^1$HNMR δ (CDCl$_3$,) ppm: 1.38 to 2.38(2H, m), 2.7 to 2.9(2H, m), 2.93 to 3.23(1H, m), 3.47 to 4.23(3H, m), 3.73(3H, s), 5.10, 5.17(2H, 2s), 7.1 to 7.5(17H, m), 8.13 to 8.35(2H, m).

Compound 7c R=methylcarbamoylamino

IR ν (CHCl$_3$) cm$^{-1}$:3445, 3310, 1685, 1602. $^1$HNMR δ (CDCl$_3$,) ppm: 1.3 to 2.3(2H, m), 2.7 to 2.92(2H, m), 2.8(3H, brs), 3.05 to 3.58(1H, m), 3.5 to 4.2(3H, m), 5.0 to 5.25(2H, m), 6.12 (1H, brs), 7.1 to 7.52(17H, m), 8.15 to 8.3(2H, m).

Compound 7d R=mesylamino

IR ν (CHCl$_3$) cm$^{-1}$: 3260, 1687, 1602. $^1$HNMR δ (CDCl$_3$) ppm: 1.2 to 2.35(2H, m), 2.65 to 2.9(2H, m), 2.96(3H, s), 2.95 to 3.6(1H, m), 3.73 to 4.35(3H, m), 5.08, 5.16(2H, 2s), 7.05 to 7.55(17H, m), 7.86, 7.95(1H, 2s), 8.1 to 8.3(2H, m).

Compound 7e' R=N-sulfamoyl-N-Pmz-amino

IR ν (CHCl$_3$) cm$^{-1}$:3370, 3245, 1727, 1687, 1601. $^1$HNMR δ (CDCl$_3$) ppm: 1.35 to 2.35(2H, m), 2.65 to 3.6(3H, m), 3.76(3H, s), 3.8 to 4.25(3H, m), 4.95 to 5.2(3H, m), 6.75 to 6.9(2H, m), 7.08 to 7.55(19H , m), 7.6 to 8.4(3H, m).

Compound 7f' R=Pmz-amino

IR ν (CHCl$_3$) cm$^{-1}$:3375, 1740, 1695, 1607. $^1$HNMR δ (CDCl$_3$) ppm: 1.35 to 2.33(2H, m), 2.65 to 3.6(3H, m), 3.79(3H, s), 3.65 to 4.2(3H, m), 4.95 to 5.25(4H, m), 6.87(2H, d, J=9 Hz), 7.07 to 7.55(19H, m), 8.1 to 8.3(3H, m).

Compound 7g R=ethylideneamino

IR ν (CHCl$_3$) cm$^{-1}$: 1692, 1600. $^1$HNMR δ (CDCl$_3$) ppm: 1.65 to 2.3(2H, m), 1.75 to 1.85(3H, m), 2.6 to 3.62(3H, m), 3.78 to 4.35(3H, m), 5.0 to 5.25(2H, m), 6.71(0.5H, q, J=5.6 Hz), 7.1 to 7.6 (17.5H, m), 8.1 to 8.3(2H, m).

C. Modification of protected amino 1  (2S,4S)-4-triphenylmethylthio-2-sulfamoylaminooxymethyl-1-p-nitrobenzyloxycarbonylpyrrolidine  (7e) (deprotection at aminooxy)

To a solution of (2S,4S)-4-triphenylmethylthio-2-N-p-methoxybenzyloxycarbonylsulfamoylaminooxymethyl-1-p-nitrobenzyloxycarbonylpyrrolidine (7e':9.2 g) in dichloromethane (100 ml) under ice cooling are added anisole (10 ml) and trifluoroacetic acid (10 ml), and the mixture is stirred for 1 hour and concentrated in vacuo. The residue is purified by silica gel chromatography to give (2S,4S)-4-triphenylmethylthio-2-sulfamoylaminooxymethyl-1-p-nitrobenzyloxycarbonylpyrrolidine (7e:5.74 g) as a yellow foam. Yield: 78%.

Compound 7e R=sulfamoylamino

IR ν (CHCl$_3$) cm$^{-1}$: 3440, 3355, 3245, 1692, 1607. $^1$HNMR δ (CDCl$_3$) ppm: 1.3 to 2.4(2H, m), 2.7 to 3.6(3H, m), 3.75 to 4.3 (3H, m), 4.9 to 5.25(3H, m), 7.08 to 7.6(17H, m), 7.6 to 7.75(1H, m), 8.1 to 8.3(2H, m).

2)  (2S,4S)-4-triphenylmethylthio-2-N-p-methoxybenzyloxycarbonyl-N-methylaminooxymethyl-1-p-nitrobenzyloxycarbonylpyrrolidine (7f'') (methylation at aminooxy)

To a suspension of sodium hydride (57.9 mg: 60% dispersion in oil) in dimethylformamide (8 ml) under ice cooling are dropwise added a solution of (2S,4S)-4-triphenylmethylthio-2-N-p-methoxybenzyloxycarbonylaminooxymethyl-1-p-nitrobenzyloxycarbonylpyrrolidine (7f':965 mg) in dimethylformamide (2 ml) and after stirring for 15 minutes methyl iodide (164 μl), and the mixture is stirred or 30 minutes. The reaction mixture is diluted with ethyl acetate, washed with water, dried over sodium sulfate, and concentrated in vacuo to give crude (2S,4S)-4-triphenylmethylhtio-2-N-p-methoxybenzyloxycarbonyl-N-methylaminooxymethyl-1-p-nitrobenzyloxycarbonylpyrrolidine (7f'':821 mg). This product can be used in the next step without further purification.

Compound 7f'' R =N-methyl-N-Pmz-amino $^1$HNMR δ CDCl$_3$) ppm: 1.7 to 2.3(2H, m), 2.6 to 3.65(3H, m), 3.08(3H, s), 3.7 to 4.2(3H, m), 3.76, 3.78(3H, 2s), 4.95 to 5.25(4H, m), 6.8 to 7.0(2H, m) 7.1 to 7.6(19H, m), 8.05 to 8.35(2H, m).

3)  (2S,4S)-4-triphenylmethylthio-2-methylaminooxymethyl-1-p-nitrobenzyl oxycarbonylpyrrolidine (7f) (deprotection at aminooxy)

To a solution of crude (2S,4S)-4-triphenylmethylthio-2-N-p-methoxybenzyloxycarbonyl-N-methylaminooxymethyl-1-p-nitrobenzyloxycarbonylpyrrolidine (7f'':821 mg) in dichloromethane (8.2 ml) under ice cooling are added anisole (1 ml) and trifluoroacetic acid (1 ml), and the mixture is stirred for 20 minutes and concentrated in vacuo. The residue is purified by silica gel chromatography to give (2S,4S)-4-triphenylmethylthio-2-N-methylaminooxymethyl-1-p-nitrobenzyloxycarbonylpyrrolidine (7f) trifluoroacetate (843 mg). Yield: 94%.

Compound 7f R=methylamino

IR ν (CHCl$_3$) cm$^{-1}$:3400, 1685, 1605. $^1$HNMR δ (CDCl$_3$) ppm: 1.47 to 2.42(2H, m), 2.65 to 3.52(3H, m), 2.84(3H, s), 4.02 to 4.45(3H, m), 5.09, 5.15(2H, 2s), 7.1 to 7.6(17H, m), 8.05 to 8.5(2H, m).

D. Deprotection at thiol (2S,4S)-4-mercapto-2-acetylaminooxymethyl-1-p-nitrobenzyloxycarbonylpyrrolidine (8a) (detritylation)

To a solution of (2S,4S)-4-tritylthio-2-acetylaminooxymethyl-1-p-nitrobenzyloxycarbonylpyrrolidine (7a:452 mg) in methanol (9 ml) under ice cooling are dropwise added pyridine (149 μl) and then a solution of silver nitrate (289 mg) in a mixture of water (1.5 ml) and methanol (15 ml), and the mixture is stirred for 25 minutes. Separating silver salt is collected by filtration, washed with methanol, ether, and petroleum ether, and dried. To a suspension of this crude silver salt in a mixture of dichloromethane (3.5 ml) and methanol (3.5 ml) is introduced hydrogen sulfide gas for 5 minutes. The resulting silver sulfide is filtered off and washed with a mixture of methanol and dichloromethane. The filtrate is concentrated in vacuo. The residue is purified by silica gel chromatography to give (2S,4S)-4-mercapto-2-acetylaminooxymethyl-1-p-nitrobenzyloxycarbonyl-pyrrolidine (8a:198 mg) as a pale yellow foam. Yield: 73%.

Under the reaction condition listed in Table 2, the protected mercaptide (7a to 7 g) is deprotected to give mercaptopyrrolidine (8a to 8 g) in a manner similar to above.

TABLE 2
Removing of mercapto protective group

|   | amino substituent in R | Solvent | pyridine equiv. | AgNO3 equiv. | Crop (%) |
|---|---|---|---|---|---|
| a | acetyl | MeOH | 2.5 | 2.3 | 73 |
| b | methoxycarbonyl | MeOH | 2.5 | 2.3 | 64 |
| c | methylcarbamoyl | MeOH | 2.5 | 2.3 | 73 |
| d | mesyl | MeOH—THF | 2.5 | 2.3 | 68 |
| e | sulfamoyl | MeOH—THF | 2.5 | 2.3 | 62 |
| f | methyl | MeOH | 3.5 | 2.3 | 50 |
| g | ethylidene | MeOH—THF | 2.5 | 2.3 | 72 |

Physical constants of mercaptopyrrolidine (8a to 8 g)

Compound 8a R=acetylamino

IR ν (CHCl3) cm$^{-1}$: 3350, 1687, 1603. $^1$HNMR δ (CDCl3-CD3OD) ppm: 1.65 to 2.15(1H, m), 1.89(3H, s), 2.52 to 2.72(1H, m), 3.1 to 3.45(2H, m), 3.95 to 4.3(4H, m), 5.23(2H, m), 7.53(2H, d, J=8.8 Hz), 8.24(2H, d, J=8.8 Hz).

Compound 8b R=carbomethoxyamino

IR ν (CHCl3) cm$^{-1}$: 3360, 1742, 1690, 1601. $^1$HNMR δ (CDCl3) ppm: 1.5 to 1.82(2H, m), 1.78(1H, d, J=6.6 Hz), 2.5 to 2.7(1H, m), 3.06 to 3.44(2H, m), 3.76(3H, s), 3.88 to 4.4(4H, m), 5.23 (2H, s) 7.52(2H, d, j=8.8 Hz), 8.23(2H, d, J=8.8 Hz).

Compound 8c R=methylcarbamoylamino

IR ν (CHCl3) cm$^{-1}$: 3440, 3325. 1683, 1602. $^1$HNMR δ (CDCl3) ppm: 1.4 to 1.9(2H, m), 1.78(1H, d, J=6.4 Hz), 2.51 to 2.69(1H, m), 2.83(3H, d, J=4.8 Hz), 3.1 to 3.47(2H, m), 3.88 to 4.4(4H, m), 5.23(2H, s), 7.52(2H, d, J=8.8 Hz), 8.23(2H, d, J=8.8 Hz).

Compound 8d R=mesylamino

IR ν (CHCl3) cm$^{-1}$:3270, 1692, 1600. $^1$HNMR δ (CDCl3) ppm: 1.45 to 1.65(1H, m), 1.79(1H, d, J=6.2 Hz), 2.5 to 2.7(1H, m), 3.01(3H, s), 3.03 to 3.5(2H, m), 3.97 to 4.5(4H, m), 5.22 (2H, s), 7.52(2H, d, J=8.8 Hz), 7.92(1H, s), 8.23(2H, d, J=8.8Hz).

Compound 8e R=sulfamoylamino

IRν (CHCl3) cm$^{-1}$:3375, 3320, 3220, 1679, 1595. $^1$HNMR δ (CDCl3) ppm: 1.45 to 1.75(1H, m), 1.81(1H, d, J=6.4 Hz), 2.5 to 2.7(1H, m), 3.1 to 3.5(2H, m), 4.0 to 4.45(4H, m), 5.21(2H, s), 5.29(2H, s), 7.52(2H, d, J=8.6 Hz), 7.77(1H, s), 8.22(2H, d, J=8.6 Hz).

Compound 8R=methylamino

IR ν (CHCl3) cm$^{-1}$: 3470, 1695, 1603. $^1$HNMR δ (CDCl3) ppm: 1.7 to 1.97(1H, m), 1.75(1H, d, J=6.6 Hz), 2.46 to 2.7(1H, m), 2.69(3H, s), 3.07 to 3.4(2H, m), 3.7 to 4.25(4H, m), 5.22 (2H, s), 7.53(2H, d, J=8.8 Hz), 8.22(2H, d, J=8.8 Hz).

Compound 8g R=ethylideneamino

IR ν (CHCl3) cm$^{-1}$: 3370, 1698, 1602. $^1$HNMR δ (CDCl3) ppm: 1.65 to 2.05(2H, m), 1.84(3H, d, J=5.8 Hz), 2.45 to 2.65 (1H, m), 3.0 to 3.4(2H, m), 3.97 to 4.5(4H, m), 5.23(2H, s), 6.75 (0.5H, q, J=5.8 Hz), 7.42(0.5H, q, J=5.8 Hz), 7.53(2H, d, J=9.0 Hz), 8.22 (2H, d, J=9.0 Hz).

E. Preparation of steroisomeric aminooxymethylpyrrolidine

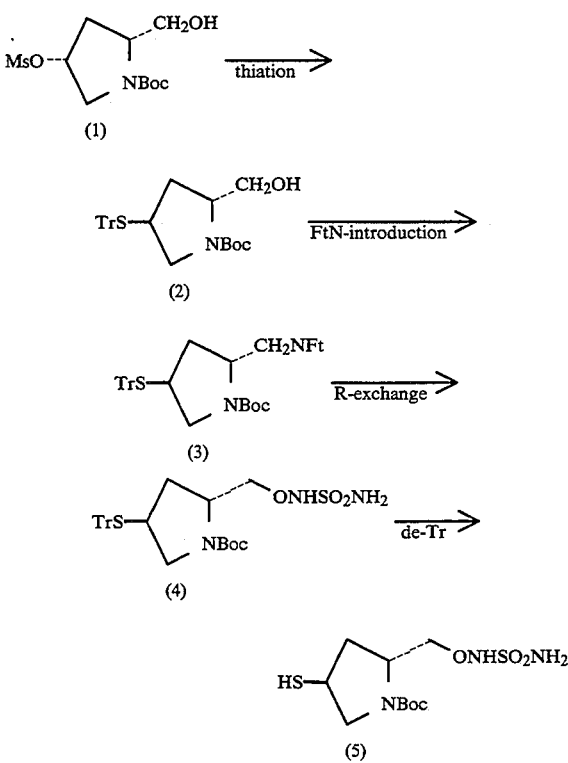

1) (2R,4S)-1-t-butoxcarbonyl-4-tritylthiopyrrolidine-2-methanol (2) (thiation)

To a solution of (2R,4R)-1-t-butoxycarbonyl-4-mesyloxypyrrolidine-2-methanol (1: 1.00 g: 3.34 mMol.) in tetrahydrofuran (3.4 ml) at room temperature is dropwise added a solution of tritylmercaptane (1.41 g: 5.09 mMol.) and sodium hydride (178 mg:4.41 mMol.) in tetrahydrofuran (8.8 ml), and the mixture is stirred at room temperature for 100 minutes. The reaction mixture is diluted with ethyl acetate (30 ml) and ice water (30 ml). The organic layer is taken, washed with water and saturated brine, dried over magnesium sulfate, and concentrated under reduced pressure. The residue is purified by silica gel chromatography to give (2R,4S)-1-t-butoxycarbonyl-4-tritylthiopyrrolidine-2-methanol (2:1.42 g). Yield : 88%.

IR ν (KBr) cm$^{-1}$: 3430, 1690. $^1$NMR δ (CDCl3) ppm: 1.2 to 1.5(m, 1H), 1.43(d, J=1.6 Hz, 9H), 1.6 to 1.9 (m, 1H), 2.7 to 3.5(m, 5H), 3.8 to 4.0(m, 1H), 7.1 to 7.6(m, 15H).

2) (2R,4S)-1-t-butoxycarbonyl-2-phtalimidooxymethyl-4-tritylthiopyrroline (3) (introduction of imidooxy)

To a solution of (2R,4S)-1-t-butoxycarbonyl-4-tritylthiopyrrolidine-2-methanol (2: 1.37 g: 2.88 mMol.) in tetrahydrofuran (8.6 ml) under ice cooling are added triphenylphosphin (892 mg: 3.40 mMol.), N-hydroxyphthalimide (705 mg: 4.32 mMol.) and azodicarboxylic acid diethyl ester (0.59 ml: 3.74 mMol.), and the mixture is stirred under ice cooling for 90 minutes. The reaction mixture is diluted with ethyl acetate (30 ml) and ice water (30 ml). The organic layer is taken, washed with water and saturated brine, dried over magnesium sulfate, and concentrated under reduced pressure. The residue is purified by silica gel chromatography to give (2R,4S)-1-t-butoxycarbonyl-2-phtalimidooxymethyl-4-tritylthiopyrrolidine (3: 1.73 g). Yield: 97%.

IR $\nu$ (KBr) cm$^{-1}$:3420, 1790, 1735, 1694. $^1$NMR $\delta$ (CDCl$_3$) ppm: 1.35(s, 9H), 1.8 to 2.4(m, 2H), 2.7 to 3.2(m, 2H), 3.8 to 4.3(m, 2H), 7.1 to 7.6(m, 15H), 7.6 to 7.9(m, 4H).

3) (2R,4S)-1-t-butoxycarbonyl-2-sulfamidooxymethyl-4-tritylthiopyrrolidine (4) (modification at aminooxy)

To a solution of (2R,4S)-1-t-butoxycarbonyl-2-phtalimidooxymethyl-4-tritylthiopyrrolidine (3:2.00 g: 3.22 mMol.) in dichloromethane (25.8 ml) in nitrogen, is dropwise added methylhydrazine 187 μl (3.54 mMol.) at −30° C. and the mixture is stirred at the same temperature for 35 minutes and under ice cooling for 25 minutes. The reaction mixture is diluted with dichloromethane (25 ml) and the separating crystals are removed by filtration. The filtrate is washed with saturated brine, dried over magnesium sulfate, and concentrated under reduced pressure. To a solution of the residue in dichloromethane (25.0 ml) at −40° C. is added a solution of triethylamine (895 μl: 6.44 mMol.) and sulfamoyl chloride (4.83 mMol.) in dichloromethane, and the mixture is stirred at −40° C. for 40 minutes, and then diluted with water (30 ml). The organic layer is taken, washed with aqueous sodium hydrogen carbonate and saturated brine, dried over magnesium sulfate, and concentrated under reduced pressure. The residue is purified by silica gel chromatography to give (2R,4S)-1-t-butoxycarbonyl-2-sulfamidooxymethyl-4-tritylthiopyrrolidine (4: 1.45 g). Yield: 81%.

IR $\nu$ (KBr) cm$^{-1}$:3400, 3240, 1670. $^1$NMR $\delta$ (CDCl$_3$) ppm: 1.1 to 1.4(m, 1H), 1.41(s, 9H), 1.6 to 1.9(m, 1H), 2.7 to 3.2(m, 3H), 3.2 to 3.9(m, 2H), 3.9 to 4.3(m,1H), 4.6 to 5.1(m, 2H), 7.1 to 7.6(m, 15H), 7.8 to 8.0(m, 1H).

4) (2R,4S)-1-t-butoxycarbonyl-2-sulfamidooxymethyl-4-mercaptopyrrolidine (5) (Deprotection at thiol)

To a solution of (2R,4S)-1-t-butoxycarbonyl-2-sulfamidooxymethyl-4-tritylthiopyrrolidine (4: 1.35 g: 2.42 mMol.) in a mixture of methanol (24.3 ml) and tetrahydrofuran (2.7 ml) under ice cooling is added a solution of pyridine (0.49 ml: 6.05 mMol.), silver nitrate (945 mg: 5.57 mMol.) in water (4.7 ml)-methanol (47.0 ml), and the mixture is stirred at the same temperature for 40 minutes, and concentrated under reduced pressure. The residue is washed with toluene and again concentrated under reduced pressure. To a solution of the residue in dichloromethane (24.2 ml)-methanol (7.3 ml) under ice cooling is bubbled hydrogen sulfide for 5 minutes. The reaction mixture is diluted with dichloromethane (30 ml), filtered to remove black precipitate, and concentrated (the filtrate) under reduced pressure. The residue is purified by silica gel chromatography to give (2R,4S)-1-t-butoxycarbonyl-2-sulfamidooxymethyl-4-mercaptopyrrolidine (5:502 mg). Yield: 64%.

IR $\nu$ (CHCl$_3$) cm$^{-1}$:3440, 3350, 3280, 1682. $^1$NMR $\delta$ (CDCl$_3$) ppm: 1.47(s, 9H), 1.6 to 1.8(m, 3H), 1.8 to 2.2(m, 1H), 3.2 to 3.5(m, 2H), 3.6 to 4.1(m, 3H), 4.2 to 4.5(m, 1H), 5.10(s, 2H), 7.8 to 8.0 (m, 1H).

EXAMPLE 2

Condensation

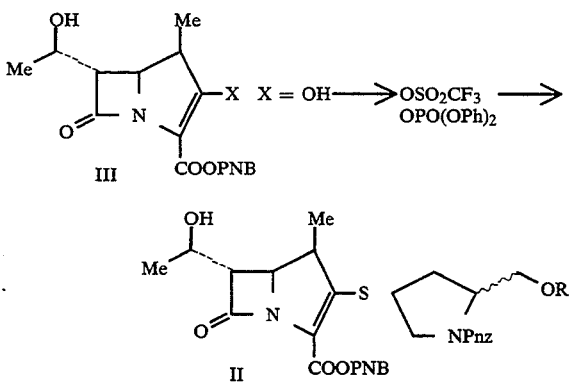

1) (1R,5S,6S)-2-[(3S,5S)-{5-acetylaminooxymethyl-1-p-nitrobenzyloxycarbonyl}pyrrolidin-3-ylthio]-6-[(1R)-1-hydroxyethyl]-1-methyl-1-carba- 2-penem-3-carboxylic acid p-nitrobenzyl ester (IIa)

To a solution of (1R,5S,6S)-2-oxo-6-[(1R)-1-hydroxyethyl]-1-methyl-1-carba-2-penem-3-carboxylic acid p-nitrobenzyl ester (154 mg) in acetonitrile (3 ml) at −40° C. are added diisopropylethylamine (89 μl) and trifluoromethanesulfonic acid anhydride (71 μl), and the mixture is stirred for 15 minutes to give a solution of (1R,5S,6S)-2-trifluoromethanesulfonyloxy-6-[(1R)-1-hydroxyethyl]-1-methyl-1-carba-2-penem-3-carboxylic acid p-nitrobenzyl ester (III).

To this solution of (III) at −40° C. is dropwise added a solution of diisopropylethylamine (89 μl) and 4-mercapto-2-acetylaminooxymethyl-1-p-nitrobenzyloxycarbonylpyrrolidine (8a:190 mg) in acetonitrile (1.5 ml), and the mixture is stirred at the same temperature for 2 hours and under ice cooling or 30 minutes and diluted with ethyl acetate. The reaction mixture is washed with water and saturated brine, dried over sodium sulfate, and concentrated in vacuo. The residue is purified by silica gel chromatography to give (1R,5S,6S)-2-[(3S,5S)-5-acetylaminooxymethyl-1-p-nitrobenzyloxycarbonylpyrrolidin-3-ylthio]-6-[(1R)-1-hydroxyethyl]-1-methyl-1-carba-2-penem-3-carboxylic acid p-nitrobenzyl ester (IIa:270 mg) as a pale yellow powder. Yield: 89%.

Under the conditions listed in Table 3, trifluoromethanesulfonate (III) is condensed with mercaptopyrrolidine (8a to 8g) by a similar handling to give the corresponding carbapenem (IIa to IIg).

TABLE 3

| Reaction conditions of condensation | | | | |
|---|---|---|---|---|
| | Product carbapenem II amino substituent in R | Starting thiol equivalents | Time (min.) at −40° C. and 0° C. | Crop (%) |
| a | acetyl | 8 a (1.2) | 120    30 | 89 |
| b | carbomethoxy | 8 b (1.2) | 30    30 | 78 |
| c | methylcarbamoyl | 8 c (1.2) | 45    40 | 83 |
| d | mesyl | 8 d (1.2) | 65    — | 82 |
| e | sulfamoyl | 8 e (1.2) | 70    35 | 72 |
| f | methyl | 8 f (1.2) | 30    30 | 63 |

TABLE 3-continued

| Product carbapenem II amino substituent in R | Reaction conditions of condensation | | |
|---|---|---|---|
| | Starting thiol equivalents | Time (min.) at −40° C. and 0° C. | Crop (%) |
| g  ethylidene | 8 g (1.2) | 25    65 | 74 |

Physical constants of protected carbapenems (II)

Compound IIa R=acetylamino

IR $\nu$ (CHCl$_3$) cm$^{-1}$: 3365, 1765, 1690, 1602. $^1$HNMR $\delta$ (CDCl$_3$) ppm: 1.28(3H, d, J=7.2 Hz), 1.37(3H, d, J=6.2 Hz), 1.4 to 2.2(3H, m), 1.91(3H, s), 2.52 to 2.7(1H, m), 3.28(1H, dd, J$_1$=6.2 Hz J$_2$=2.6 Hz), 3.22 to 3.45(2H, m), 3.55 to 4.48(7H, m), 5.23, 5.50(2H, ABq, J=13.7 Hz), 5.24(2H, s), 7.52(2H, d, J=8.8 Hz), 7.65(2H, d, J=8.8 Hz), 8.22 (2H, d, J=8.8 Hz), 8.23(2H, d, J=8.8 Hz).

Compound IIb R=carbomethoxyamino

IR $\nu$ (CHCl$_3$) cm$^{-1}$: 3375, 1765, 1695, 1602. $^1$HNMR $\delta$ (CDCl$_3$) ppm: 1.28(3H, d, J=7.2 Hz), 1.37(3H, d, J=6.2 Hz), 1.64 (2H, brs), 1.7 to 1.9(1H, m), 2.48 to 2.72(1H, m), 3.28(1H, dd, J$_1$=6.2 Hz, J$_2$=2.6 Hz), 3.22 to 3.43(2H, m), 3.58 to 3.82(1H, m), 3.76(3H, s), 3.9 to 4.45(6H, m), 5.23, 5.50(2H, ABq, J=13.7 Hz), 5.23(2H, s), 7.52 (2H, d, J=8.8 Hz), 7.65(2H, d, J=8.8 Hz), 8.23(2H, d, J=8.8 Hz), 8.24(2H, d, J=8.8 Hz).

Compound IIc R=methylcarbamoylamino

IR $\nu$ (CHCl$_3$) cm$^{-1}$: 3440, 3380, 3330, 1767, 1685, 1601. $^1$HNMR $\delta$ (CDCl$_3$) ppm: 1.26(3H, d, J=7.4 Hz), 1.37(3H, d, J=6.2 Hz), 1.73 (3H, brs), 2.42 to 2.75(1H, m), 2.83(3H, d, J=4.8 Hz), 3.2 to 3.45(2H, m), 3.28(1H, dd, J$_1$=6.2 Hz, J$_2$=2.6 Hz), 3.58 to 4.47(7H, m), 5.22, 5.51 (2H, ABq, J=13.0 Hz), 5.23(2H, s), 7.52(2H, d, J=8.8 Hz), 7.65(2H, d, J=8.8 Hz), 8.22(2H, d, J=8.8 Hz), 8.23(4H, d, J=8.8 Hz).

Compound IId R=mesylamino

IR $\nu$ (CHCl$_3$) cm$^{-1}$: 3410, 3280, 3190, 1768, 1698, 1602. $^1$HNMR $\delta$ (CDCl$_3$) ppm: 1.29(3H, d, J=7.2 Hz), 1.37(3H, d, J=6.8 Hz), 1.73 to 2.13 (1H, m), 1.98(2H, s), 2.54 to 2.78(1H, m), 3.03(3H, s), 3.29(1H, dd, J$_1$=6.8 Hz, J$_2$=2.6 Hz), 3.2 to 3.5(2H, m), 3.62 to 4.5(7H, m), 5.22(2H, s), 5.22, 5.50(2H, ABq, J=13.6 Hz), 7.43 to 7.66(2H, m), 7.65(2H, d, J=8.8 Hz), 8.22(2H, d, J=8.8 Hz), 8.24(2H, d, J=8.8 Hz).

Compound IIe R=sulfamoylamino

IR $\nu$ (KBr) cm$^{-1}$: 3390, 3235, 3105, 3080, 1762, 1696, 1602. $^1$HNMR $\delta$ (CDCl$_3$-CD$_3$OD) ppm: 1.27(3H, d, J=7.2 Hz), 1.34(3H, d, J=6.2 Hz), 1.77 to 2.2(1H, m), 2.35 to 2.78(1H, m), 3.27(1H, dd, J$_1$=6.2 Hz, J$_2$=2.6 Hz), 3.3 to 3.46(2H, m), 3.63 to 3.82(1H, m), 3.97 to 4.4(6H, m), 5.22 (2H, s), 5.24, 5.48(2H, ABq, J=13.7 Hz), 7.47 to 7.62(2H, m), 7.66(2H, d, J=8.8 Hz), 8.22(2H, d, J=8.8 Hz), 8.23(2H, d, J=8.8 Hz).

Compound IIf R=methylamino

IR $\nu$ (CHCl$_3$) cm$^{-1}$: 3390, 1767, 1697, 1602. $^1$HNMR $\delta$ (CDCl$_3$) ppm: 1.28(3H, d, J=7.8 Hz), 1.37(3H, d, J=6.8 Hz), 1.75 to 2.15 (1H, m), 2.38 to 2.7(1H, m), 2.68(3H, s), 3.15 to 3.53(2H, m), 3.27(1H, dd, J$_1$=6.8 Hz, J$_2$=2.6 Hz), 3.5 to 4.35(7H, m), 5.23(2H, s), 5.23, 5.51(2H, ABq, J=13.2 Hz), 7.53 (2H, d, J=8.8 Hz), 7.65 (2H. d, J=8.8 Hz), 8.22(4H, d, J=8.8 Hz).

Compound IIg R=ethylideneamino

IR $\nu$ (CHCl$_3$) cm$^{-1}$:3370, 1768, 1700, 1603. $^1$HNMR $\delta$ (CDCl$_3$) ppm: 1.28(3H, d, J=7.0 Hz), 1.37(3H, d, J=6.4 Hz), 1.65(1H, brs), 1.82(3/2H, d, J=5.6 Hz), 1.83(3/2H, d, J=5.6 Hz), 1.9 to 2.2(½H, m), 2.4 to 2.65(½H, m), 3.15 to 3.75(4H, m), 3.9 to 4.4(7H, m), 5.25(2H, s), 5.24, 5.52(2H, ABq, J=14 Hz), 6.75(½H, q, J=5.6 Hz), 7.40(½H, q, J=5.6 Hz), 7.54(2H, d, J=8.8 Hz), 7.66(2H, d, J=8.8 Hz), 8.23(2H, d, J=8.8 Hz).

2) (1R,5S,6S)-2-[(3S,5R)-1-t-butoxycarbonyl-5-sulfamidooxymethylpyrrolidin-3-ylthio]-6-[(1R)-1-hydroxyethyl]-1-methyl-1-carba-2-penem-3-carboxylic acid diphenylmethyl ester To a solution of (1R,5S,6S)-2-diphenoxyphosphonyloxy-6-[(1R)-1-hydroxyethyl]-1-methyl-1-carba-2-penem-3-carboxylic acid diphenylmethyl ester (832 mg:1.33 mMol.) and (2R,4S)-1-t-butoxycarbonyl-2-sulfamidooxymethyl-4-mercaptopyrrolidine (522 mg:1.59 mMol.) in acetonitrile (4.2 ml) in nitrogen under ice cooling is dropwise added a solution of disopropylethylamine (0.30 ml:1.73 mMol.) in acetonitrile (2.1 ml), and the mixture is stirred at the same temperature for 3 hours. The mixture is diluted with ethyl acetate (30 ml) and ice water (30 ml). The organic layer is taken, washed with water and saturated brine, dried over magnesium sulfate, and concentrated under reduced pressure. The residue is purified by silica gel chromatography to give (1R,5S,6S)-2-[(3S,5R)-1-t-butoxycarbonyl-5-sulfamidooxymethylpyrrolidin-3-ylthio]-6-[(1R)-1-hydroxyethyl]-1-methyl-1-carba-2-penem-3-carboxylic acid diphenylmethyl ester (843 mg). Yield: 90%.

IR $\nu$ (KBr) cm$^{-1}$:3390, 3240, 1765. $^1$NMR $\delta$ (CDCl$_3$) ppm: 1.26(d, J=7.2 Hz, 3H), 1.42(s, 9H), 3.1 to 3.5(m, 2H), 3.52~4.4(m, 5H), 5.22 to 5.4(m, 1H), 5.6 to 5.8(m, 1H), 6.93(s, 1H), 7.1 to 7.7(m, 10H), 7.7 to 7.9(m, 1H). UV $\lambda$ max: 321 nm.

EXAMPLE 3

Deprotection

1) Deprotections to afford (3S,5S)-mercaptopyrrolidine isomers

To a solution of (1R,5S,6S)-2-[(3S,5S)-R substituted aminooxymethyl-1-p-nitrobenzyloxycarbonylpyrrolidine-4-ylthio)-6-[(1R)-1-hydroxyethyl]-1-methyl-1-carba-2-penem-3-carboxylic acid p-nitrobenzyl ester (IIa: 1 part) in a mixture of tetrahydrofuran (15 volume) and 0.05M 2-(morpholin-4-yl)ethanesulfonic acid buffer (pH 6.86:30 volume) is added 10% palladium/carbon (1 weight), and the mixture is shaken at room temperature under a hydrogen atmosphere for 2 to 3 hours. The reaction mixture is filtered to remove catalyzer and the filtrate is washed with dichloromethane and ether and passed through a column of styrene-divinyl benzene copolymer resin absorbent. The absorbed material is eluted with aqueous 10% methanol. The eluate is lyophilized to give (1R,5S,6S)-2-[(3S,5S)-5-R substituted aminooxymethylpyrrolidin-3-ylthio]-6-[(1R)-1-hydroxyethyl]-1-methyl-1-carba-2-penem-3-carboxylic acid (Ia). Yield: 20 to 56%.

By a similar handling, protected 2-[(3S,5S)-5-R substituted aminooxymethylpyrrolidin-3-ylthio]-carbapenems (IIa to IIg) are deprotected under the same condition as above to give the corresponding carbapenems (Ia to Ig).

Physical constants of carbapenem (I)

Compound Ia R: acetylamino

IR $\nu$ (KBr) cm$^{-1}$: 3410, 1748, 1672, 1583. UV $\lambda_{max}$ $\epsilon$ (H$_2$O) nm: 297 (9700). $^1$HNMR $\delta$ (D$_2$O) ppm: 1.21(3H, d, J=7.4 Hz), 1.28(3H, d, J=6.4 Hz), 1.68 to 1.84(1H, m), 1.94(3H, s), 2.62 to 2.8(1H, m), 3.29 to 3.47(2H, m), 3.46(1H, dd, J$_1$=6.4 Hz, J$_2$=2.6 Hz), 3.66 to 3.77(1H, m), 3.96 to 4.14(2H, m), 4.16 to 4.32(4H, m).

This compound shows potent: prevention of infection in mice caused by e.g., Staphylococcus aureus Smith (0.099 mg/kg) and Pseudomonas aeruginosa SR24 (0.58 mg/kg).

Compound Ib R=carbomethoxyamino

IR $\nu$ (KBr) cm$^{-1}$: 3420, 1748, 1588. UV $\lambda_{max}$ $\epsilon$ (H$_2$O) nm: 297 (9600). $^1$HNMR $\delta$ (D$_2$O) ppm: 1.21(3H, d, J=7.2 Hz), 1.28(3H, d, J=6.2 Hz), 1.65 to 1.85(1H, m), 2.62 to 2.81(1H, m), 3.28 to 3.55(2H, m), 3.46(1H, dd, J$_1$=6.2 Hz, J$_2$=2.6 Hz), 3.65 to 3.77(1H, m), 3.76(3H, s), 3.97 to 4.15(2H, m), 4.1 to 4.3(4H, m).

This compound shows potent prevention of infection in mice caused by e.g., Staphylococcus aureus Smith (0.11 mg/kg) and Pseudomonas aeruginosa SR24 (0.57 mg/kg).

Compound Ic R=methylcarbamoylamino

IR $\nu$ (KBr) cm$^{-1}$: 3380, 1755, 1663, 1587, 1545. UV $\lambda_{max}$ $\epsilon$ (H$_2$O) nm: 297 (9600). $^1$HNMR $\delta$ (D$_2$O) ppm: 1.21(3H, d, J=7.2 Hz), 1.28(3H, d, J=6.0 Hz), 1.64 to 1.78(1H, m), 2.61 to 2.8(1H, m), 2.76(3H, s), 3.29 to 3.45(2H, m), 3.46(1H, dd, J$_1$=6.0 Hz, J$_2$=2.6 Hz), 3.59 to 3.72(1H, m), 3.93 to 4.31(6H, m).

This compound shows potent prevention of infection in mice caused by e.g., Staphylococcus aureus Smith (0.057 mg/kg) and Pseudomonas aeruginosa SR24 (0.40 mg/kg).

Compound Id R=methanesulfonylamino

IR $\nu$ (KBr) cm$^{-1}$: 3410, 1750, 1585. UV $\lambda_{max}$ $\epsilon$ (H$_2$O) nm: 297 (9600). $^1$HNMR $\delta$ (D$_2$O) ppm: 1.21(3H, d, J=7.4 Hz), 1.28(3H, d, J=6.2 Hz), 1.62 to 1.82(1H, m), 2.63 to 2.78(1H, m), 3.18(3H, s), 3.27 to 3.44(2H, m), 3.46(1H, dd, J$_1$=6.2 Hz, J$_2$=2.8 Hz), 3.56 to 3.69(1H, m), 3.91 to 4.15(2H, m), 4.13 to 4.34(4H, m). Elemental Analysis Calcd.: C, 43.16; H, 6.15; N, 9.44; S, 14.40. (C$_{16}$H$_{25}$N$_3$O$_7$S$_2$.0.54H$_2$O) Found: C, 42.95; H, 6.05; N, 9.73; S, 14.12.

This compound shows potent antibacterial activity in vitro against e.g., Escherichia coli SR5028 (0.05 μg/ml) and Pseudomonas aeruginosa PAO1-Jdg (0.01 μg/ml); and a high urinay recovery in mice (38.6%).

Compound Ie R:=sulfamoylamino

IR $\nu$ (KBr) cm$^{-1}$: 3300, 3210, 1749, 1588. UV $\lambda_{max}$ $\epsilon$ (H$_2$O) nm: 297 (9400). $^1$HNMR $\delta$ (D$_2$O) ppm: 1.21(3H, d, J=7.4 Hz), 1.28(3H, d, J=6.2 Hz), 1.6 to 1.78(1H, m), 2.58 to 2.77(1H, m), 3.25 to 3.46(2H, m), 3.45(1H, dd, J$_1$=6.2 Hz, J$_2$=2.6 Hz), 3.53 to 3.65(1H, m), 3.89 to 4.1(2H, m), 4.13 to 4.35(4H, m). Elemental Analysis Calcd.: C, 40.43; H, 5.66; N, 12.58; S, 14.39. (C$_{15}$H$_{24}$N$_4$O$_7$S$_2$0.5H$_2$O) Found: C, 40.23; H, 5.88; N, 12.58; S, 14.30.

This compound shows potent antibacterial activity in vitro against e.g., Escherichia coli SR5028 (0.05 μg/ml) and Pseudomonas aeruginosa A25619 (0.1 μg/ml) and SR1012 (0.4 μg/ml); potent prevention of infection in mice caused by e.g., Staphylococcus aureus Smith (0.038 mg/kg) and Pseudomonas aeruginosa SR24 (0.20 mg/kg); and a high urinay recovery in mice (45%).

Compound If R=methylamino

IR $\nu$ (KBr) cm$^{-1}$: 3400, 3260, 1751, 1592. UV $\lambda_{max}$ $\epsilon$ (H$_2$O) nm: 297(9000). $^1$HNMR $\delta$ (D$_2$O) ppm: 1.21(3H, d, J=7.4 Hz), 1.28(3H, d, J=6.2 Hz), 1.64 to 1.83(1H, m), 2.67(3H, s), 2.6 to 2.8(1H, m), 3.29 to 3.45(2H, m), 3.46(1H, dd, J$_1$=6.2 Hz, J$_2$=2.6 Hz), 3.58 to 3.72(1H, m), 3.9 to 4.08(4H, m), 4.17 to 4.33(2H, m).

This compound shows potent antibacterial activity in vitro against: e.g., Escherichia coli H (0.05 μg/ml) and a high urinay recovery in mice (52.1%).

Compound Ig R=ethylideneamino (E:Z=1:1)

IR $\nu$ (EBr) cm$^{-1}$:3420, 1757, 1590. UV $\lambda_{max}$ $\epsilon$ (H$_2$O) nm: 297(9300). $^1$HNMR $\delta$ (D$_2$O) ppm: 1.22(3H, d, J=7.2 Hz), 1.28(3H, d, J=6.2 Hz), 1.7 to 1.9(1H, m), 1.86, 1.89(3H, 2 d, J$_1$=6.0 Hz, J$_2$=5.6 Hz, 2.62 to 2.82(1H, m), 3.26 to 3.47(2H, m), 3.44 to 3.52(1H, m), 3.57 to 3.75(1H, m), 3.92 to 4.17(2H, m), 4.15 to 4.48(4H, m), 7.0, 7.62(1H, 2q, J$_1$=5.6 Hz, J$_2$=6.0 Hz).

This compound shows potent anti bacterial activity in vitro against e.g., Pseudomonas aeruginosa PA01-Jdg (0.02 μg/ml): high maximum blood level in mice (27.7 μg/ml): and a high urinay recovery in mice (39.4%).

2) Deprotection to afford (3S,5R)-mercaptopyrrolidine isomer

To a solution of (1R,5S,6S)-2-[(3S,5R)-1-t-butoxycarbonyl-5-sulfamidooxymethylpyrrolidin-3-ylthio]-6-[(1 R)-1-hydroxyethyl]-1-methyl-1-carba-2-penem-3-carboxylic acid diphenylmethyl ester (800 mg: 1.14 mMol.) in dichloromethane (4.6 ml) at −35° C. is dropwise added a solution of aluminum chloride (1.22 g: 9.12 mMol.) in a mixture of dichloromethane (9.1 ml)-anisole (9.1 ml)-nitromethane (9.1 ml), and the mixture is stirred at the same temperature for 3 hours. The reaction mixture is diluted a solution of sodium acetate (2.25 g) in water (23 ml). The aqueous layer is taken, washed with dichloromethane and purified by column chromatography over styrene-divinylbenzene copolymer to give (1R, 5S, 6S)-2-[(3S,5R)-5-sulfamidooxymethylpyrrolidin-3-ylthio]-6-[(1R)-1-hydroxyethyl]-1-methyl-1-carba-2-penem-3-carboxylic acid (364 mg). Yield: 73%.

IR $\nu$ (KBr) cm$^{-1}$:3400, 1750. $^1$NMR $\delta$ (D$_2$O) ppm: 1.18(d, J=7.0 Hz, 3H), 1.24(d, J=6.4 Hz, 3H), 2.12 to 2.4(m, 2H), 3.22 to 3.5(m, 3H), 3.68(dd, J=5.4 Hz, J=12.4 Hz, 1H), 4.0 to 4.4(m, 6H). UV $\lambda$ max: 296 nm.

This compound shows potent antibacterial activity in vitro against e.g., Morgaia morganii SR9 (0.2 μg/ml) and Pseudomonas aeruginosa A25619 (0.1 μg/ml), and Pseudomonas aeruginosa SR1012 (0.4 μg/ml).

EXAMPLE 4

Modification at the pyrrolidine nitrogen

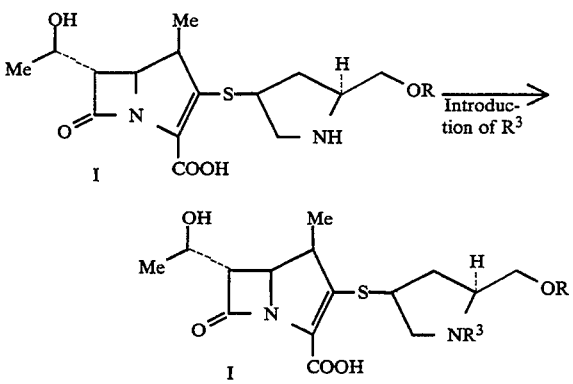

(1R,5S,6S)-2-[(3S,5S)-1-iminomethyl-5-methanesulfonylaminooxymethylpyrrolidin-3-ylthio]-6-[(1R)-1-hydroxyethyl]-1-methyl-1-carba-2-penem-3-carboxylic acid (Ih)

To a solution of (1R,5S,6S)-2-[(3S,5S)-5-methanesulfonylaminooxymethylpyrrolidin-3-ylthio]-6-[(1R)-1-hydroxyethyl]-1-methyl-1-carba-2-penem-3-carboxylic acid (Id:62 mg) in a phosphate buffer (15 ml) of pH 7.1 under ice cooling are added 1N-sodium hydroxide and ethylformimidate hydrochloride (270 mg) in several portions while keeping the reaction medium at pH 8.5, and the mixture is stirred at the same temperature for 25 minutes. The reaction mixture is adjusted to pH 7.0 with 1N-hydrochloric acid, purified by chromatography on styrene-divinylbenzene copolymer, and lyophilized to give (1R,5S,6S)-2-[(3S,5S)-5-methanesulfonylaminooxymethylpyrrolidin-3-yl-thio]-6-[(1R)-1-hydroxyethyl]-1-methyl-1-carba-2-penem-3-carboxylic acid (Ih:49 mg) as colorless foam. Yield: 63%.

Compound Ih R=iminomethyl, R=amino

IR $\nu$ (KBr) cm[1]: 3360, 1748, 1701, 1630. 1582. UV $\lambda_{max}\epsilon$ (H$_2$O) nm: 297 (8700). $^1$HNMR $\delta$ (D$_2$O) ppm: 1.21(3H, d, J=7.4 Hz), 1.29(3H, d, J=6.2 Hz), 1.8 to 2.03 (1H, m), 2.6 to 2.85(1H, m), 3.14(3H, s), 3.3 to 3.6(2H, m), 3.46 (1H, dd, J$_1$=6.2 Hz. J$_2$=2.8 Hz), 3.88 to 4.52(7H, m), 8.08(1H, s).

EXAMPLE 5

Stereoisomers at position 5 of pyrrolidinylthio

In a manner similar to those of Examples 1 to 4, the stereoisomers (1R,5S,6S)-2-[(3R,5S)-5-acetamidooxymethylpyrrolidin-3-yl-thio]-6-[(1R)-1-hydroxyethyl]-1-methyl-1-carba-2-penem-3-carboxylic acid, (1R,5S,6S)-2-[(3R,5R)-5-methylcarbamoylaminooxymethylpyrrolidin-3-ylthio]-6-[(1R)-1-hydroxyethyl]-1-methyl-1-carba-2-penem-3-carboxylic acid, (1R,5S,6S)-2-[(3R,5S)-5-sulfamoylaminooxymethylpyrrolidin-3-yl-thio]-6-[(1R)-1-hydroxyethyl]-1-methyl-1-carba-2-penem-3-carboxylic acid, (1R,5S,6S)-2-[(3R,5R)-5-sulfamoylaminooxymethylpyrrolidin-3-ylthio]-6-[(1R)-1-hydroxyethyl]-1-methyl-1-carba-2-penem-3-carboxylic acid (1R,5S,6S)-2-[(3R 5)-5-methanesulfonylaminooxymethylpyrrolidin-3-yl-thio]-6-[(1R)-1-hydroxyethyl]-1-methyl-1-carba-2-penem-3-carboxylic acid, and (1R,5S,6S)-2-[(3R,5R)-5-methanesulfonylaminooxymethylpyrrolidin-3-ylthio]-6-[(1R)-1-hydroxyethyl]-1-methyl-1-carba-2-penem-3-carboxylic acid are prepared from the stereoisomers at position 4 of (D or L)-hydroxyproline.

Formulation Example 1

(injection)

Sodium salt of (1R,5S,6S)-2-[(3S,5S)-5-methanesulfonylaminooxy-methylpyrrolidin-3-ylthio]-6-[(1R)-1-hydroxyethyl]-1-methyl-1-carba-2-penem-3-carboxylic acid (1 g) in a 5 ml vial is dissolved in sterilized water for injection (1 ml) before use and given by intravenus injection thrice a day to an adult patient suffering from pyelitis.

Formulation Example 2

(infusion)

An aqueous solution of sodium (1R,5S,6S)-2-[(3S,5S)-5-sulfamidooxymethylpyrrolidin-3-ylthio]-6-[(1R)-1-hydroxyethyl]-1-methyl-1-carba-2-penem-3-carboxylate (1 g) adjusted to pH 7.5 with sodium hydrogen carbonate is placed in a 150 ml bottle and lyophilized. The lyophilizate is dissolved in sterilized water for injection (100 ml) and dripped intravenously to an adult patient immediately after or during a surgical operation for preventing post operative bacterial infection.

Formulation Example 3

(suspension)

Microcrystalline (1R,5S,6S)-2-[(3S,5R)-5-sulfamidooxymethylpyrrolidin-3-ylthio]-6-[(1R)-1-hydroxyethyl]-1-methyl-1-carba-2-penem-3carboxylic acid (2 g) in a 5 ml vial is suspended in sterilized water (3 ml) for injection, and given intramuscularly twice a day to an adult patient suffering from suppurative inflammation.

Experiment

Stability against human renal dehydropeptidase-1

A solution (1 $\mu$l) of test carbapenem compound (50 $\mu$g) in 50 mM-tris-hydrochloric acid buffer (pH 7.5:1 ml) is added to a solution of human renal dehydropeptidase-1 in 50 mM tris-hydrochloric acid buffer (pH 7.5:0.33 unit/ml:10 $\mu$l), and the mixture is stirred at 37° C. for 60 minutes. The reaction is quenched with methanol (10 $\mu$l) and diluted with 0.1M phosphate buffer (pH 7.0:80 $\mu$l). The remaining antibacterial potency of this solution is measured.

Among compounds I, Id (R=methanesulfonylamino) showed 71% and Ie (R=sulfamoylamino) showed 78%.

In contrast, known compounds, (5R,6S)-2-(formimidoylaminoethylthio-6-[(1R)-1-hydroxyethyl]-1-carba-2-penem-3-carboxylic acid (imipenem), (5R,6S)-2-[1-(1-acetoimidoyl)pyrrolidin-3-ylthio]-6-[(1R)-1-hydroxyethyl]carba-2-penem-3-carboxylic acid (CS533) and (1R,5S,6S)-2-[(3S,5S)-5-dimethylaminocarbonylpyrrolidin-3-ylthio]-6-[(1R)-1-hydroxyethyl]-1-methyl-1-carba-2-penem-3-carboxylic acid (Meropenem) showed values of 51%, 48%, and 69%, respectively.

What we claim is:

1. An aminooxypyrrolidinylthiocarbapenem compound of Formula I, and pharmaceutically acceptable salts thereof:

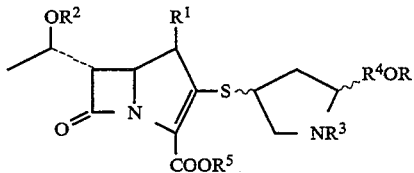

wherein R is an amino group which is optionally substituted by a 1C to 10C monovalent amino substituent selected from the group consisting of alkyl, acetyl, alkoxycarbonyl, N-methylcarbamoyl, alkylsulfonyl and sulfamoyl; or R is an amino group which is substituted by a 1C to 10C divalent amino substituent selected from the group consisting of alkylidene and phthalyl;

R$^1$ is hydrogen or a 1C to 5C alkyl;

R$^2$ is hydrogen or a conventional hydroxy protecting group;

R$^3$ is hydrogen or an imino protecting group;

R$^4$ is a 1C to 5C alkylene;

R$^5$ is hydrogen or a conventional carboxy protecting group; and each wavy line represents a bond in an R or S configuration.

2. A compound claimed in claim 1 wherein the stereochemistry in the pyrrolidine ring is either in a (2S,4R) or (2S,4S)-configuration.

3. A compound claimed in claim 1 wherein R$^1$ is methyl.

4. A compound claimed in claim 1 wherein R$^4$ is methylene.

5. A compound claimed in claim 1 wherein R$^2$ is hydrogen or a tri-1C to 4C alkylsilyl.

6. A compound claimed in claim 1 wherein $R^3$ is hydrogen.

7. A compound claimed in claim 1 wherein $R^5$ is hydrogen or an alkali metal.

8. A compound in claim 1 wherein R is methanesulfonylamino, or sulfamoylamino.

9. A compound claimed in claim 1 wherein

R is amino, $R^1$ is methyl, $R^2$ and $R^3$ are hydrogens, $R^4$ is methylene, and $R^5$ is hydrogen;

R is a acetylamino, $R^1$ is methyl, $R^2$ and $R^3$ are hydrogens, $R^4$ is methylene, and $R^5$ is hydrogen;

R is carbomethoxyamino, $R^1$ is methyl, $R^2$ and $R^3$ are hydrogens, $R^4$ is methylene, and $R^5$ is hydrogen;

R is methylcarbamoylamino, $R^1$ is methyl, $R^2$ and $R^3$ are hydrogens, $R^4$ is methylene, and $R^5$ is hydrogen;

is methanesulfonylamino, $R^1$ is methyl, $R^2$ and $R^3$ are hydrogens, $R^4$ is methylene, and $R^5$ is hydrogen;

R is sulfamoylamino, $R^1$ is methyl, $R^2$ and $R^3$ are hydrogens, $R^4$ is methylene, and $R^5$ is hydrogen;

R is methylamino, $R^1$ is methyl, $R^2$ and $R^3$ are hydrogens, $R^4$ is methylene, and $R^5$ is hydrogen; or R is ethylideneamino, $R^1$ is methyl, $R^2$ and $R^3$ are hydrogens, $R^4$ is methylene, and $R^5$ is hydrogen;

or a pharmaceutically acceptable alkali metal salt thereof, provided that its stereochemistry at the pyrrolidine ring is (2S,4R)- or (2S,4S).

10. An antibacterial agent containing a compound claimed in claim 1 as an active ingredient.

11. A pharmaceutical formulation containing an antibacterially effective amount of a compound claimed in claim 1 as an active ingredient, and a pharmaceutically acceptable carrier therefor.

12. A method for combatting a bacteria by contacting said bacteria with a compound claimed in claim 1.

13. A method for combating a bacteria as recited in claim 12, wherein the bacteria is a gram-negative bacteria.

14. An antibacterial agent containing a compound claimed in claim 1 as an active ingredient.

15. A pharmaceutical formulation containing an antibacterially effective amount of a compound claimed in claim 9 as an active ingredient, and a pharmaceutically acceptable carrier therefor.

16. A method for combatting a bacteria by contacting said bacteria with a compound claimed in claim 9.

17. A method for combatting a bacteria as recited in claim 9, wherein the bacteria is a gram-negative bacteria.

* * * * *

UNITED STATES PATENT AND TRADEMARK OFFICE
CERTIFICATE OF CORRECTION

PATENT NO.  : 5,360,798
DATED       : November 1, 1994
INVENTOR(S) : Sendo, et. al.

It is certified that error appears in the above-indentified patent and that said Letters Patent is hereby corrected as shown below:

Title page, item [75], inventor: change "Kii Makoto" to Makoto Kii--.

Signed and Sealed this

Third Day of January, 1995

Attest:

BRUCE LEHMAN

*Attesting Officer*   *Commissioner of Patents and Trademarks*